United States Patent
Kurimura et al.

(10) Patent No.: US 8,048,258 B2
(45) Date of Patent: Nov. 1, 2011

(54) RESIN COMPOSITION, AND TEMPORARY FIXING METHOD AND SURFACE PROTECTING METHOD FOR MEMBERS TO BE PROCESSED, BY MEANS THEREOF

(75) Inventors: Hiroyuki Kurimura, Shibukawa (JP);
Tomoyuki Kanai, Shibukawa (JP);
Kazuhiro Oshima, Shibukawa (JP)

(73) Assignee: Denki Kagaku Kogyo Kabushiki Kaisha, Tokyo (JP)

( * ) Notice: Subject to any disclaimer, the term of this patent is extended or adjusted under 35 U.S.C. 154(b) by 500 days.

(21) Appl. No.: 12/297,316

(22) PCT Filed: May 24, 2007

(86) PCT No.: PCT/JP2007/060618
§ 371 (c)(1),
(2), (4) Date: Oct. 16, 2008

(87) PCT Pub. No.: WO2007/148506
PCT Pub. Date: Dec. 27, 2007

(65) Prior Publication Data
US 2009/0196987 A1 Aug. 6, 2009

(30) Foreign Application Priority Data
Jun. 19, 2006 (JP) .................. 2006-168635

(51) Int. Cl.
*C04B 37/00* (2006.01)
*B65B 35/00* (2006.01)
*C09D 5/00* (2006.01)
*C08L 33/24* (2006.01)

(52) U.S. Cl. .......... 156/325; 427/154; 525/218
(58) Field of Classification Search .......... 156/325; 427/154; 525/218
See application file for complete search history.

(56) References Cited

U.S. PATENT DOCUMENTS

| 3,057,816 | A | | 10/1962 | Armen et al. |
| 3,057,817 | A | | 10/1962 | Armen et al. |
| 3,097,185 | A | | 7/1963 | Armen et al. |
| 5,624,998 | A | * | 4/1997 | Itoh et al. .................. 524/812 |
| 2003/0158076 | A1 | * | 8/2003 | Rodrigues .................. 510/475 |

* cited by examiner

*Primary Examiner* — Philip Tucker
*Assistant Examiner* — Michael Orlando
(74) *Attorney, Agent, or Firm* — Oblon, Spivak, McClelland, Maier & Neustadt, L.L.P.

(57) ABSTRACT

To provide a resin composition for e.g. a temporary fixing adhesive which has a high adhesive strength and which is readily removable in water, and a temporary fixing method for a member by means thereof.

A resin composition comprising component (A): N,N-diethylacrylamide and/or N-isopropylacrylamide, component (B): at least one member selected from the group consisting of a homopolymer of N-vinyl-2-pyrrolidone, a homopolymer of N,N-dimethylacrylamide, a homopolymer of N,N-diethylacrylamide, a homopolymer of acryloylmorpholine, a homopolymer of N-isopropylacrylamide, and a copolymer of at least two monomers selected from the group consisting of N-vinyl-2-pyrrolidone, N,N-dimethylacrylamide, N,N-diethylacrylamide, acryloylmorpholine and N-isopropylacrylamide, and component (C): a polymerization initiator. A temporary fixing method for a member and a surface protecting method for a member, by means the resin composition.

9 Claims, No Drawings

RESIN COMPOSITION, AND TEMPORARY FIXING METHOD AND SURFACE PROTECTING METHOD FOR MEMBERS TO BE PROCESSED, BY MEANS THEREOF

TECHNICAL FIELD

The present invention relates to a temporary fixing method and a surface protecting method for various members to be processed at the time of processing them, and a resin composition and adhesive suitable for such methods.

BACKGROUND ART

When semiconductor wafers, optical components, etc. are to be made thin, it is common to process them by a so-called rear surface grinding method wherein a circuit surface of a wafer or a surface to be processed of an optical component is protected by a surface protecting sheet, and the protected wafer or component is temporarily fixed to a substrate via the surface protecting sheet, and the rear surface opposite to the circuit surface is ground.

At present, the wall thickness of a wafer is usually 150 μm at an industrial level, however, a thinner wafer is desired. When a wafer is to be made thinner, a phenomenon wherein the ground surface (the rear surface) tends to be non-uniform by an influence of irregularities of the circuit surface, i.e. a rear surface transfer phenomenon of the circuit pattern, tends to be distinct.

The cause for such a rear surface transfer phenomenon may be explained as follows. A pressure sensitive adhesive surface-protecting sheet presently available is limited in its conformability to circuit irregularities of a semiconductor wafer. Therefore, there will be spaces (air pockets) between the adhesive layer and the circuit surface, and the wafer at such regions are not directly supported by the adhesive layer (protective layer). When the wafer is to be made very thin by grinding, at the non-supported scribe line (street), the wafer tends to move in a vertical direction between the circuit and the die while compressing the air pocket, and consequently, such a region will not be ground and will be thicker than other portions. On the other hand, in a case where a hard projection such as a bump is present, the wafer will be ground more, and consequently, such a portion will be thinner than other portions.

Such a phenomenon will not be problematic when the finishing thickness of the wafer is at least 150 μm. However, in a case where the wafer is to be made thinner than 100 μm (particularly when it is to be finished to have a thickness of at most 50 μm) or in a case where a projection such as a bump on the wafer circuit surface is very large (e.g. when it is at least 100 μm), not only the deflecting strength of the wafer is thereby substantially decreased, but also the wafer may be broken during the grinding in an extreme case.

In a case where a wafer is to be ground to be thin at a level of about 50 μm, chipping of the edge of the wafer or penetration of the grinding water between the wafer and the surface protecting layer will, for example, be problematic, and the cause is again due to a defect in adhesion of the surface protecting sheet to the edge of the wafer. Further, with a semiconductor wafer having a projection of at least 100 μm represented by a bump on the circuit surface, not only the thinning of the wafer, but also grinding itself tends to be difficult which is carried out by bonding a typical semiconductor surface protecting sheet.

A conventional surface protecting sheet is usually a sheet having an adhesive layer as a surface protecting layer on a polymer film material. The adhesive is designed so that it has a low elastic modulus so that it will conform to irregularities of the circuit surface. However, if such a tendency is too much, when the sheet is to be peeled off from the wafer, a large stress will be exerted to the wafer, thus leading to breakage.

Accordingly, an energy ray-facilitated release type protecting sheet has been developed whereby before peeling the sheet, the adhesive is cured by irradiation with energy rays such as ultraviolet rays to decrease the bond strength between the wafer and the protecting sheet. However, if the adhesive layer is in a non-cured state during the grinding, there is a problem that it is so flexible that the wafer will be broken during the grinding.

The Patent Document 1 discloses a method for grinding a wafer wherein an energy ray-facilitated release type protecting sheet as described above, is bonded on a wafer having a circuit formed, and the adhesive layer is cured by energy rays, whereupon grinding of the rear surface of the wafer is carried out. However, the adhesive is not a fluid, whereby the conformability to irregularities on the wafer circuit is surface is not sufficient.

Patent Document 2 discloses a hot melt type semiconductor surface-protecting sheet. The hot melt type sheet to be melted to show fluidity when heated to a level of from 60 to 100° C., conforms to irregularities on the circuit surface to present excellent grinding properties. However, this sheet has such a nature that it melts every time when the temperature becomes higher than the melting point.

On the other hand, a semiconductor wafer may usually be subjected to e.g. a heating step between a step of bonding a die attachment film (hereinafter referred to also as "DAF") i.e. a film to be used for fixing a chip after the wafer is bonded to the protecting sheet and a step of forming a metal film by sputtering. Therefore, by the temperature rise in such a step, there has been a trouble such that the protecting sheet will be melted again.

Patent Document 1: JP-A-11-026406
Patent Document 2: JP-A-2000-38556

DISCLOSURE OF THE INVENTION

Object to be Accomplished by the Invention

It is an object of the present invention to provide a photocurable adhesive which has a high adhesive strength in order to improve the dimensional accuracy of a member after grinding and which is excellent in release properties in water and also environmentally excellent in the working efficiency free from an adhesive remaining on the member after the removal. Particularly in a case where semiconductor wafers, optical components, etc. are to be made thin by a rear surface grinding method, the object of the present invention is to provide a photocurable adhesive having the above characteristics, which protects a circuit surface of a wafer or a non-processed surface of an optical component.

Means Accomplish the Object

In order to solve the problems of the prior art and to satisfy the above-mentioned demands of industry, the present inventors have conducted various studies to obtain a composition which is a material having sufficient conformability to irregularities on the circuit surface of a wafer or an optical component and which has a sufficient rigidity as a support at the time of grinding, and as a result, have found that it is possible to obtain an adhesive composition which has a high adhesive strength and which has a good release property in water by using a specific substance i.e. N,N-diethylacrylamide and/or N-isopropylacrylamide and by combining it with a specific hydrophilic polymer, and it is thereby possible to accomplish the above object. The present invention has been accomplished on the basis of such a discovery.

Further, at the time of processing e.g. an optical member, the present invention presents a surface protecting method for a member to be processed, for the purpose of protecting a portion not to be processed on the surface of the member to be processed from e.g. fouling, and presents also a temporary fixing method for a member to be processed which comprises bonding such an object to be processed to a substrate, processing the object and then dipping the bonded portion to remove the cured product thereby to recover the member to be processed. Further, the present invention presents a resin composition and an adhesive suitable for such a method.

Thus, the present invention provides the following:
1. A resin composition comprising component (A): N,N-diethylacrylamide and/or N-isopropylacrylamide, component (B): at least one member selected from the group consisting of a homopolymer of N-vinyl-2-pyrrolidone, a homopolymer of N,N-dimethylacrylamide, a homopolymer of N,N-diethylacrylamide, a homopolymer of acryloylmorpholine, a homopolymer of N-isopropylacrylamide, and a copolymer of at least two monomers selected from the group consisting of N-vinyl-2-pyrrolidone, N,N-dimethylacrylamide, N,N-diethylacrylamide, acryloylmorpholine and N-isopropylacrylamide, and component (C): a polymerization initiator.
2. The resin composition according to the above 1, which contains component (D): a polymerization inhibitor.
3. The resin composition according to the above 1 or 2, wherein component (A) is contained in an amount of from 1 to 99 parts by mass per 100 parts by mass of the total amount of components (A) and (B).
4. The resin composition according to any one of the above 1 to 3, wherein component (C) is contained in an amount of from 0.1 to 20 parts by mass per 100 parts by mass of the total amount of components (A) and (B).
5. The resin composition according to any one of the above 2 to 4, wherein component (D) is contained in an amount of from 0.001 to 3 parts by mass per 100 parts by mass of the total amount of components (A) and (B).
6. The resin composition according to any one of the above 1 to 5, wherein component (B) is a homopolymer of N-vinyl-2-pyrrolidone, or a copolymer containing at least N-vinyl-2-pyrrolidone.
7. An adhesive made of the resin composition as defined in any one of the above 1 to 6.
8. A cured product of the resin composition as defined in any one of the above 1 to 6, which has a solubility in water or swells upon absorption of water.
9. A temporary fixing method for a member, which comprises temporarily fixing a member by means of the resin composition as defined in any one of the above 1 to 6, processing the temporarily fixed member, and then dipping the processed member in water to remove the cured product of the resin composition.
10. A surface protecting method for a member, which comprises applying and curing the resin composition as defined in any one of the above 1 to 6, on a surface of a member, and then dipping the member in water to remove the cured product of the resin composition.

Effect of the Invention

The resin composition of the present invention has a high water-absorbing property because of its composition, whereby the swelling property or solubility of the cured product is high, and the release property from the adherend is good, and the solubility of the cured product itself in water is high, or the resin composition has both of such characteristics. Accordingly, by using the resin composition of the present invention, a member may be bonded and temporarily fixed, and the temporarily fixed member may be processed, and then, the processed member may simply be dipped in water to be freed. Further, the viscosity adjustment of the adhesive before the curing is easy, and by optionally adjusting the viscosity, depending upon the shape of an article, its space may be filled with the resin composition of the present invention.

The temporary fixing method and the surface protecting method for a member of the present invention employs the resin composition, of which the adhesive strength is reduced simply in contact with water, and they are characterized in that simply by contacting the bonded portion with water, the member can easily be recovered. Thus, as compared with a conventional adhesive, a remarkable effect can be obtained such that it is not necessary to employ an organic solvent which is expensive and highly flammable or which generates a gas harmful to a human body.

BEST MODE FOR CARRYING OUT THE INVENTION

In the present invention, component (A) is N,N-diethylacrylamide and/or N-isopropylacrylamide.

Further, in the present invention, component (B) is at least one member selected from the group consisting of a homopolymer of N-vinyl-2-pyrrolidone, a homopolymer of N,N-dimethylacrylamide, a homopolymer of N,N-diethylacrylamide, a homopolymer of acryloylmorpholine, a homopolymer of N-isopropylacrylamide, and a copolymer of at least two monomers selected from the group consisting of N-vinyl-2-pyrrolidone, N,N-dimethylacrylamide, N,N-diethylacrylamide, acryloylmorpholine and N-isopropylacrylamide. In the present invention, as component (B), a homopolymer of N-vinyl-2-pyrrolidone or a copolymer containing at least N-vinyl-2-pyrrolidone is preferred.

Further, in the present invention, component (C) is a polymerization initiator.

In the resin composition of the present invention, the compositional ratio of component (A) to component (B) may optionally be determined depending upon the desired viscosity. Namely, the viscosity may be adjusted to a desired level by changing the blend amount of component (B) so that in order to increase the viscosity, component (B) is increased, and in order to lower the viscosity, the component (B) is decreased. In such a case, it is preferred that component (A) is adjusted to be from 1 to 50 parts by mass per 100 parts by mass of the total amount of components (A) and (B). Further, for example, in an application to a portion where a space is large or in an application to a bent member, it is preferred that the resin composition is adjusted to have a high viscosity and in such a case, component (A) is preferably adjusted to be from 50 to 99 parts by mass per 100 parts by mass of the total amount of components (A) and (B).

The polymerization initiator as component (C) may, for example, be a photopolymerization initiator or a redox polymerization initiator. As the photopolymerization initiator, various known photopolymerization initiators may be used. Specifically, benzophenone or its derivative; benzyl or its derivative; anthraquinone or its derivative; benzoin or a benzoin derivative such as benzoin methyl ether, benzoin ethyl ether, benzoin propyl ether, benzoin isobutyl ether or benzyl dimethyl ketal; an acetophenone derivative such as diethoxyacetophenone or 4-t-butyltrichloroacetophenone; 2-dimethylaminoethyl benzoate, p-dimethylaminoethyl benzoate, diphenyl disulfide, thioxanthone or its derivative; camphorquinone or a camphorquinone derivative such as 7,7-dimethyl-2,3-dioxobicyclo[2.2.1]heptane-1-carboxylic acid, 7,7-dimethyl-2,3-dioxobicyclo[2.2.1]heptane-1-carboxy-2-bromoethylester, 7,7-dimethyl-2,3-dioxobicyclo[2.2.1]heptane-1-carboxy-2-methylester or 7,7-dimethyl-2,3-dioxobicyclo[2.2.1]heptane-1-carboxylic acid chloride; an α-aminoalkylphenone derivative such as 2-methyl-1-[4-(methylthio)phenyl]-2-morpholinopropan-1-one or 2-benzyl-2-dimethylamino-1-(4-morpholinophenyl)-butanone-1; or an acylphosphine oxide derivative such as benzoyldiphenylphosphine oxide, 2,4,6-trimethylbenzoyldiphenylphosphine oxide, benzoyldiethoxyphosphine oxide, 2,4,6-trimethylbenzoyldimethoxyphenylphosphine oxide or 2,4,6-trimethylbenzoyldiethoxyphenylphosphine oxide, may, for example, be mentioned. Such photopolymerization initiators may be used alone or in combination as a mixture of two or more of them. As the photopolymerization initiator, benzyl dimethyl ketal or 2-methyl-1-[4-(methylthio)phenyl]-2-morpholinopropan-1-one is preferred, Further, as the above-mentioned redox polymerization initiator, a redox catalyst containing an organic peroxide and a reducing agent, is preferred. For example, a combination of a ketone peroxide such as methyl ethyl ketone peroxide or methyl cyclohexanone peroxide, with a metal soap such as cobalt naphthenate or copper naphthenate; a combination of a diacylperoxide such as octanoyl peroxide or benzoyl peroxide, with a tertiary amine such as N,N-dimethylaniline or N,N-dimethyl-p-toluidine; or a combination of cumene hydroperoxide or diisopropylbenzene hydroxide, with an organic thiourea such as thiourea, ethylenethiourea or acetylthiourea, may, for example, be mentioned. Further, it is possible to use a photopolymerization initiator and a redox polymerization initiator in combination.

The blend ratio of component (C): a polymerization initiator, is preferably from 0.1 to 20 parts by mass per 100 parts by mass of the total amount of components (A) and (B). The blend ratio of component (C) is more preferably from 0.2 to 10 parts by mass. When the blend ratio of component (C) is at least 0.1 part by mass, the effect to promote curing can certainly be obtained. When the blend ratio of component (C) is not more than 20 parts by mass, a sufficient curing speed can be obtained. In a more preferred embodiment, component (C) may be added in an amount of at least 0.2 part by mass, whereby the crosslinking degree of the cured product of the composition will be high, and dislocation or the like during the grinding can be avoided, or the release property will be improved.

The resin composition of the present invention may contain a small amount of component (D): a polymerization inhibitor in order to improve the storage stability. Such a polymerization inhibitor may, for example, be methylhydroquinone, hydroquinone, 2,2-methylene-bis(4-methyl-6-tert-butylphenol), catechol, hydroquinone monomethyl ether, mono-tert-butyl hydroquinone, 2,5-ditert-butylhydroquinone, p-benzoquinone, 2,5-diphenyl-p-benzoquinone, 2,5-di-tert-butyl-p-benzoquinone, picric acid, citric acid, phenothiazine, tert-butyl catechol, 2-butyl-4-hydroxyanisole or 2,6-di-tert-butyl-p-cresol. Among them, 2,2-methylene-bis(4-methyl-6-tert-butylphenol) is preferred as the polymerization inhibitor.

The blend ratio of such a polymerization inhibitor is preferably from 0.001 to 3 parts by mass, more preferably from 0.01 to 2 parts by mass, per 100 parts by mass of the total amount of components (A) and (B). When the blend ratio of the polymerization inhibitor is at least 0.001 part by mass, the storage stability can be secured, and when it is not more than 3 parts by mass, a good adhesive property can be obtained, and non-curing can be avoided.

In the present invention, a polar organic solvent may be used together. By using a polar organic solvent together, it is possible to more certainly let such a phenomenon take place that the composition after curing will readily be swelled in contact with water whereby the bond strength will be decreased.

With respect to the polar organic solvent, its boiling point is preferably from 50° C. to 200° C. It is preferred to select a polar organic solvent having a boiling point within the above range, whereby it is possible to make more certain a phenomenon such that the composition after curing is in contact with warm water whereby the bond strength will be decreased. As such a polar organic solvent, an alcohol, a ketone or an ester may, for example, be mentioned. Among them, an alcohol is preferably selected for use as the polar organic solvent.

The above alcohol may, for example, be methanol, ethanol, n-propanol, isopropanol, n-butanol, isobutanol, secondary butanol, tertiary butanol, n-amylalcohol, isoamylalcohol or 2-ethylbutyl alcohol. The above alcohol is preferably methanol, ethanol, n-propanol, isopropanol, n-butanol, isobutanol, secondary butanol or tertiary butanol, having a boiling point of not higher than 120° C., and methanol, ethanol, isopropanol or n-butanol is particularly preferred.

The blend ratio of the polar organic solvent is preferably from 0.5 to 10 parts by mass, per 100 parts by mass of the total amount of components (A) and (B). When the blend ratio is at least 0.5 part by mass, the release property can be secured, and when it is at most 10 parts by mass, the cured product of the composition can be peeled without a trouble of deterioration of the initial adhesive property.

In the present invention, a granular substance insoluble in components (A), (B) and (C) may be used together with components (A), (B) and (C). The composition after curing can thereby maintain a constant thickness, whereby processing accuracy will be improved.

The granular substance insoluble in components (A), (B) and (C) may be either organic or inorganic particles. Specifically, organic particles may, for example, be polyethylene particles, polypropylene particles, crosslinked polymethyl methacrylate particles or crosslinked polystyrene particles. The organic particles may, for example, be ceramic particles such as glass, silica, alumina or titanium.

The granular substance insoluble in components (A), (B) and (C) is preferably spherical with a view to improvement of processing precision i.e. control of the film thickness of the adhesive. Specifically, the organic particles are preferably crosslinked polymethyl methacrylate particles or crosslinked polystyrene particles obtainable as monodispersed particles by a known emulsion polymerization method of a methyl methacrylate monomer or a styrene monomer with a crosslinkable monomer, and the inorganic particles are preferably spherical silica, since the film thickness of the composition after curing will be uniform without substantial deformation of particles or fluctuation of the particle size. Among them, crosslinked polymethyl methacrylate particles or crosslinked polystyrene particles are more preferred from the viewpoint of the reactivity of the composition or the storage stability such as sedimentation of particles.

The blend ratio of the granular substance insoluble in components (A), (B) and (C) is preferably from 0.1 to 20 parts by mass, particularly preferably from 0.1 to 10 parts by mass, per 100 parts by mass of the total amount of components (A) and (B). When the above blend ratio is at least 0.1 part by mass, the film thickness of the composition after curing is substantially constant, and when it is at most 20 parts by mass, the initial adhesive property will not deteriorate.

The resin composition of the present invention may contain various elastomers such as acrylic rubber, urethane rubber or an acrylonitrile-butadiene-styrene rubber, or an additive such as an inorganic filler, a solvent, a bulking agent, a reinforcing material, a plasticizer, a thickener, a dye, a pigment, a flame retardant, a silane coupling agent or a surfactant.

Next, the present invention provides a temporary fixing method for a member, which comprises temporary fixing a member by means of the resin composition which loses the adhesive strength in contact with water, and after processing the temporarily fixed member, the processed member is dipped in water to remove the cured product of the above resin composition, whereby it is possible to process various members such as optical members with high processing accuracy without using an organic solvent.

Further, according to a preferred embodiment of the present invention, a cured product is in contact with water, and swells and dissolves upon absorption of water, and thus, the cured product of the composition can be removed, and it is possible to obtain an effect that the embodiment is excellent from the viewpoint of both environment and operation efficiency. Here, in the present invention, "the cured product swells upon absorption of water" means a swelled state upon absorption of water in an amount of at least 10 parts by mass per 100 parts by mass of the cured product before absorption of water.

In the temporarily fixing method of the present invention, the above-mentioned effects of the invention can certainly be obtained when an adhesive made of the above-mentioned resin composition of the present invention is used.

In the present invention, it is preferred to employ warm water heated to a proper level, specifically warm water of at most 90° C., whereby the releasing in water can be accomplished in a short time, such being preferred from the viewpoint of the production efficiency. With respect to the temperature of the above-mentioned warm water, it is preferred to employ warm water of from 30° C. to 90° C., preferably from 40° C. to 90° C., whereby the cured product of the adhesive will swell and dissolve in a short time, so that the cured product of the adhesive can be removed. Here, with respect to a method for contacting the cured product with water, a method of dipping the entire bonded assembly in water is recommended as being simple and convenient.

In the present invention, there is no particular limitation with respect to the material of the member to be used for temporary fixing, and in a case where an ultraviolet curable adhesive is used, a member made of a material capable of transmitting ultraviolet rays, is preferred. As such a material, quartz material, glass material or plastic material may, for example, be mentioned, and the temporary fixing method of the present invention is applicable to temporary fixing in processing of quartz oscillators, glass lenses, plastic lenses or optical disks.

In the temporary fixing method, with respect to a method of using an adhesive, in a case where a photocurable adhesive is employed as the adhesive, there may, for example, be mentioned a method wherein a suitable amount of the adhesive is applied to one of members to be fixed or the bonding surface of the support substrate, and then the other member is overlaid, or a method wherein plural members to be temporarily fixed are preliminarily laminated, and the adhesive is applied by letting it penetrate into clearances, and after the application of the adhesive, the members are irradiated with visible light or ultraviolet rays to cure the photocurable adhesive to temporarily fix the members to each other.

Then, the temporarily fixed members are subjected to processing such as cutting into a desired shape, grinding, polishing or drilling, and then, the members are dipped in water, preferably warm water, whereby the cured product of the adhesive can be removed from the members.

Further, the present invention provides a surface protecting method for a member to be processed, which comprises applying and curing the above resin composition on a surface of the member to be processed, and then dipping the member in water after processing, to remove the cured product of the resin composition. Namely, by applying and curing the above resin composition on the surface of the member not to be subjected to processing, it is possible to prevent chipping or fouling of the surface during the processing.

Further, according to a preferred embodiment of the present invention, the cured product is contacted with water, and it swells or dissolves, whereby the cured product of the resin composition can be removed, and an effect can be obtained such that the embodiment is excellent from the viewpoint of both environment and operation efficiency.

In the present invention, there is no particular limitation with respect to the material of the member to be used for protecting the surface, and in a case where an ultraviolet-curable adhesive is used, a member made of a material capable of transmitting ultraviolet rays is preferred. Such a material may, for example, be quartz material, glass material or plastic material, and the surface protecting method of the present invention is applicable to the surface protection in processing of quartz oscillators, glass lenses, plastic lenses and optical disks.

EXAMPLES

Now, the present invention will be described in further detail with reference to Examples and Comparative Examples. However, it should be understood that the present invention is by no means restricted to such Examples.

Example 1

A resin composition was prepared by blending 50 parts by mass of N,N-diethylacrylamide (DEAA, manufactured by KOHJIN Co., Ltd.) as component (A), 50 parts by mass of polyvinylpyrrolidone (polyvinylpyrrolidone K-30, manufactured by NIPPON SHOKUBAI CO., LTD.) as component (B), 2 parts by mass of 1-907:2-methyl-1-[4-(methylthio) phenyl]-2-morpholinopropan-1-one (IRGACURE 907, manufactured by Ciba Specialty Chemicals, hereinafter referred to as "IRGACURE 907") as the polymerization initiator for component (C) and 0.1 part by mass of 2,2-methylene-bis(4-methyl-6-tert-butylphenol) (hereinafter referred to as "MDP") as the polymerization inhibitor for component (D). Using the obtained resin composition, measurement of the tensile shear bond strength, a delamination test, a surface protecting film-delamination test and a surface hardening test were carried out by the following evaluation methods. The results are shown in Table 1.

Evaluation Methods

Tensile shear bond strength: Measured in accordance with JIS K6850. Specifically, using heat resistant Pyrex (registered trademark, the same applies hereinafter) glass (25 mm×25 mm×2.0 mm) as an adherend, two sheets of such heat resistant Pyrex glass were bonded by the composition prepared as described above, with the bonded portion being 8 mm in diameter, and the composition was cured by a curing apparatus manufactured by Fusion using an electrodeless discharge lamp, under a condition of an integral amount of light with a wavelength of 365 nm being 2,000 mJ/cm$^2$, to prepare a test specimen for tensile shear bond strength. The prepared test specimen was subjected to measurement of the tensile shear bond strength by means of a universal tester at a temperature of 23° C. in an environment of humidity of 50% at a tensile speed of 10 mm/min.

Delamination test: The composition was cured under the same condition as described above except that the resin composition was applied to the above heat resistant Pyrex glass, which was then bonded to a blue sheet glass (150 mm×150 mm×1.7 mm) as a support, to prepare a delamination test sample. The obtained test sample was immersed in warm water (80° C.), and the time until the heat resistant Pyrex (registered trademark) glass had delaminated, was measured.

Surface protecting film-delamination test: On a blue sheet glass of 150 mm×150 mm×1.7 mm, the above resin composition was applied in a thickness of 50 µm by a bar coater, and the resin composition was cured by a black light manufactured by Stanley under a condition of illuminance of 5 mW/cm$^2$ so that the integral dose of radiation would be 1,000 mJ, to prepare a test sample for surface protecting film-delamination. The obtained test sample was immersed in warm water (80° C.), and the time until the cured product had completely delaminated, was measured.

Surface hardening test: The surface of a delamination test sample B cured under the above conditions was evaluated by palpation.
○: No fingerprint observed
x: Fingerprint observed Examples 2 to 9

A resin composition was prepared in the same manner as in Example 1 except that raw materials of the types shown in Table 1 were used in the composition as shown in Table 1. With respect to the obtained composition, measurement of the tensile shear bond strength, a delamination test, a surface protecting film-delamination test and a surface hardening test were carried out in the same manner as in Example 1. The results are shown in Table 1.

Materials Used

BDK: benzyl dimethyl ketal (IRGACURE 651, manufactured by Ciba Specialty Chemicals)

NIPAM: N-isopropylacrylamide (NIPAM, manufactured by KOHJIN Co., Ltd.)

Polyvinylpyrrolidone K-30: Polyvinylpyrrolidone (K-30, manufactured by NIPPON SHOKUBAI CO., LTD.)

Polyvinylpyrrolidone K-85: Polyvinylpyrrolidone (K-85, manufactured by NIPPON SHOKUBAI CO., LTD.)

Polyvinylpyrrolidone K-90: Polyvinylpyrrolidone (K-90, manufactured by NIPPON SHOKUBAI CO., LTD.)

Examples 10 to 13

Delamination test samples A and B were prepared in the same manner as in Example 1 by using the resin compositions of Examples 2 and 6, and delamination tests and surface protecting film-delamination tests were carried out by changing the temperature of warm water to 40° C., 50° C., 60° C. and 70° C. The results are shown in Table 2. As a result, a delamination property was observed at any temperature.

TABLE 1

|  |  | Example No. | | | | | | | | |
| --- | --- | --- | --- | --- | --- | --- | --- | --- | --- | --- |
|  |  | Ex. 1 | Ex. 2 | Ex. 3 | Ex. 4 | Ex. 5 | Ex. 6 | Ex. 7 | Ex. 8 | Ex. 9 |
| Component (A) (parts by mass) | DEAA | 50 | 30 | 90 | 50 | 50 | — | — | 25 | 25 |
|  | NIPAM | — | — | — | — | — | 50 | 90 | 25 | 25 |
| Component (B) (parts by mass) | K-30 | 50 | 70 | 10 | — | — | 50 | 10 | 50 | 25 |
|  | K-85 | — | — | — | 50 | — | — | — | — | 25 |
|  | K-90 | — | — | — | — | 50 | — | — | — | — |
| Component (C) | BDK | — | — | — | — | — | 2 | 4 | — | — |
| polymerization initiator (parts by mass) | I-907 | 2 | 3 | 2 | 2 | 2 | — | — | 2 | 2 |
| Polymerization inhibitor | MDP | 0.1 | 0.1 | 0.1 | 0.1 | 0.1 | 0.1 | 0.1 | 0.1 | 0.1 |
| Bond strength (MPa) | — | — | 14.1 | 10.9 | 18.1 | 15.2 | 16.7 | 13.9 | 8.9 | 15.2 | 11.4 |
| Delamination time in warm water of 80° C. (min) | — | — | 120 | 100 | 85 | 100 | 120 | 160 | 120 | 100 | 118 |
| Delamination time of surface protecting film in warm water of 80° C. (min) | — | — | 10 | 20 | 7 | 30 | 40 | 50 | 10 | 10 | 15 |
| Surface hardening | — | — | ○ | ○ | ○ | ○ | ○ | ○ | ○ | ○ | ○ |

TABLE 2

| | Resin composition No. | | Temperature of warm water (° C.) | | | |
|---|---|---|---|---|---|---|
| | | | 40 | 50 | 60 | 70 |
| Example 10 | Example 2 | Delamination time in warm water (min) | 300 | 260 | 200 | 160 |
| Example 11 | Example 6 | Delamination time in warm water (min) | 400 | 300 | 230 | 190 |
| Example 12 | Example 2 | Delamination time of surface protecting film in warm water (min) | 100 | 80 | 60 | 30 |
| Example 13 | Example 6 | Delamination time of surface protecting film in warm water (min) | 120 | 100 | 80 | 60 |

Example 14

Using the resin composition of Example 2, heat resistant Pyrex glass of 150 mm×150 mm×2 mm and a blue sheet glass used in Example 1, as dummy glass, were bonded and cured in the same manner as in Example 1. Only the heat resistant Pyrex glass portion of this bonded test sample was cut into a 10 mm square by using a dicing machine. During the cutting, no falling of the heat resistant Pyrex glass was observed and thus good processability was shown. The bonded test sample obtained by cutting only the heat resistant Pyrex glass portion was immersed in warm water of 80° C., whereby the sample was wholly delaminated in 60 minutes. Ten such delaminated cut out test specimens were randomly taken out, and the rear side (the side temporarily fixed by the resin composition) of each cut out test specimen was observed by means of an optical microscope, whereby the maximum width of a chipped portion of the glass was measured, and the average value and the standard deviation were obtained. The results are shown in Table 3.

TABLE 3

| Test specimen No. | Maximum widths of chipped portions on the rear sides of ten cut out test specimens (μm) | | | | | | | | | | Average | Standard deviation |
|---|---|---|---|---|---|---|---|---|---|---|---|---|
| | 1 | 2 | 3 | 4 | 5 | 6 | 7 | 8 | 9 | 10 | | |
| Example 14 | 52 | 43 | 49 | 46 | 57 | 61 | 22 | 45 | 43 | 53 | 47.1 | 10.1 |
| Comparative Example 1 | 41 | 57 | 80 | 53 | 44 | 48 | 55 | 89 | 76 | 99 | 64.2 | 19.2 |
| Comparative example 2 | 45 | 50 | 90 | 111 | 77 | 99 | 80 | 100 | 110 | 131 | 89.3 | 25.7 |

Comparative Example 1

A hot melt type adhesive (ADFIX A, manufactured by NIKKA SEIKO CO., LTD.) was heated and dissolved at 90° C., and heat resistant Pyrex glass of 150 mm×150 mm×2 mm and the blue sheet glass used in Example 1, were bonded. Only the heat resistant Pyrex glass portion of this bonded test sample was cut into a 10 mm square by means of a dicing apparatus. During the cutting, no falling of the heat resistant Pyrex glass was observed, and good processability was shown. The test specimen was immersed in an N-methylpyrrolidone solution for 1 day, and the cut out test specimen was recovered. In the same manner as in Example 14, ten such delaminated cut out test specimens were randomly taken out, and the rear side (the side temporarily fixed by the hot melt type adhesive) of each cut out test specimen was observed by using an optical microscope, whereby the maximum widths of chipped portions of the glass were measured, and the average value and the standard deviation were obtained. The results are shown in Table 3.

Comparative Example 2

Using an UV-curable PET adhesive tape, heat resistant Pyrex glass of 150 mm×150 mm×2 mm was bonded. Only the heat resistant Pyrex glass portion of this bonded test sample was cut into a 10 mm square by means of a dicing apparatus. The adhesive tape portion of such a test specimen was irradiated with ultraviolet rays to lower the bond strength, whereupon the cut out test specimen was recovered. In the same manner as in Example 14, ten such delaminated cut out specimens were randomly taken out, and the rear side (the side temporarily fixed by the adhesive tape) of each cut out test specimen was observed by using an optical microscope, whereby the maximum widths of chipped portions of glass were measured, and the average value and the standard deviation were obtained. The results are shown in Table 3.

INDUSTRIAL APPLICABILITY

The resin composition of the present invention provides a high bond strength to prevent displacement of a member during the processing and thus presents such an effect that a member excellent in dimensional accuracy can easily be obtained. Further, the resin composition of the present invention loses the adhesive strength in contact with water, whereby the bond strength between members or between a member and a jig will decrease thereby to facilitate the recovery of the member or members. The resin composition of the present invention is industrially useful as an adhesive for temporary fixing and a surface protecting material for e.g. optical lenses, prisms, arrays, silicon wafers or semiconductor mount components.

The temporary fixing method for a member of the present invention employs the resin composition having such characteristics, whereby it is unnecessary to use an organic solvent which used to be required in the prior art, and thus is industrially very useful.

The entire disclosure of Japanese Patent Application No. 2006-168635 filed on Jun. 19, 2006 including specification, claims and summary is incorporated herein by reference in its entirety.

The invention claimed is:

1. A resin composition, comprising:
   (A): N,N-diethylacrylamide, N-isopropylacrylamide, or a mixture thereof;
   (B): at least one member selected from the group consisting of a homopolymer of N-vinyl-2-pyrrolidone, a homopolymer of N,N-dimethylacrylamide, a homopolymer of N,N-diethylacrylamide, a homopolymer of acryloylmorpholine, a homopolymer of N-isopropylacrylamide, and a copolymer of at least two monomers selected from the group consisting of N-vinyl-2-pyrrolidone, N,N-dimethylacrylamide, N,N-diethylacrylamide, acryloylmorpholine and N-isopropylacrylamide; and
   (C): a polymerization initiator;
   wherein an amount of (A) is from 30 to 99 parts by mass per 100 parts by mass of a total amount of (A) and (B).

2. The resin composition according to claim 1, further comprising (D): a polymerization inhibitor.

3. The resin composition according to claim 1, wherein an amount of (C) the polymerization initiator is from 0.1 to 20 parts by mass per 100 parts by mass of the total amount of components (A) and (B).

4. The resin composition according to claim 2, wherein an amount of (D) the polymerization inhibitor is from 0.001 to 3 parts by mass per 100 parts by mass of the total amount of components (A) and (B).

5. The resin composition according to claim 1, wherein (B) is a homopolymer of N-vinyl-2-pyrrolidone, or a copolymer comprising N-vinyl-2-pyrrolidone.

6. An adhesive comprising the resin composition as defined in claim 1.

7. A cured product of the resin composition as defined in claim 1, which has a solubility in water or swells upon absorption of water.

8. A method for processing a member, comprising:
   temporarily fixing a member to a surface of a support substrate with a cured product of the resin composition as defined in claim 1;
   processing the temporarily fixed member; and then
   dipping the processed fixed member in water to remove the cured product of the resin composition.

9. A method to temporarily protect a member, comprising:
   applying and curing the resin composition as defined in claim 1, on a surface of a member, and then
   dipping the member in water to remove the cured product of the resin composition.

* * * * *